US012569201B2

(12) United States Patent
Johnson et al.

(10) Patent No.: US 12,569,201 B2
(45) Date of Patent: Mar. 10, 2026

(54) ADVANCED PLAY ENVIRONMENT FOR SCREENING AND EARLY DIAGNOSIS OF INFANT DEVELOPMENTAL DELAYS AND NEUROLOGICAL IMPAIRMENTS

(71) Applicants: The Trustees of the University of Pennsylvania, Philadelphia, PA (US); The Children's Hospital of Philadelphia, Philadelphia, PA (US)

(72) Inventors: Michelle Johnson, Philadelphia, PA (US); Laura Prosser, Yardley, PA (US); Daniel Bogen, Philadelphia, PA (US); Helen Loeb, Wynnewood, PA (US); Roshan Rai, Lansdale, PA (US)

(73) Assignees: The Trustees of the University of Pennsylvania, Philadelphia, PA (US); The Children's Hospital of Philadelphia, Philadelphia, PA (US)

( * ) Notice: Subject to any disclaimer, the term of this patent is extended or adjusted under 35 U.S.C. 154(b) by 1385 days.

(21) Appl. No.: 16/877,149

(22) Filed: May 18, 2020

(65) Prior Publication Data

US 2021/0022682 A1 Jan. 28, 2021

Related U.S. Application Data

(63) Continuation of application No. 15/376,072, filed on Dec. 12, 2016, now abandoned.
(Continued)

(51) Int. Cl.
*A61B 5/00* (2006.01)
*A61B 5/11* (2006.01)
(Continued)

(52) U.S. Cl.
CPC .......... *A61B 5/6896* (2013.01); *A61B 5/1125* (2013.01); *A61B 5/1128* (2013.01);
(Continued)

(58) Field of Classification Search
CPC ... A61B 5/4082; A61B 5/6892; A61B 5/7275; A61B 5/7405; A61B 5/742; A61B 2562/0219; A61B 2562/0247
See application file for complete search history.

(56) References Cited

U.S. PATENT DOCUMENTS

| | | | |
|---|---|---|---|
| 8,961,438 B2 | 2/2015 | Gravem et al. | |
| 2010/0007717 A1 | 1/2010 | Spektor et al. | |

(Continued)

FOREIGN PATENT DOCUMENTS

WO WO 2007/043036 A1 4/2007

OTHER PUBLICATIONS

U.S. Appl. No. 14/012,466 (U.S. Pat. No. 9,232,912) filed Aug. 28, 2013 (Jan. 12, 2016).
(Continued)

*Primary Examiner* — Alex M Valvis
*Assistant Examiner* — Yasmeen S Warsi
(74) *Attorney, Agent, or Firm* — Baker Botts L.L.P.

(57) ABSTRACT

The presently disclosed subject matter relates to a play environment for children and infants for detecting motor delays or impairments, evaluating neurological development, and for diagnosing developmental disorders, and methods and systems of using the same.

16 Claims, 17 Drawing Sheets

Related U.S. Application Data

(60) Provisional application No. 62/266,378, filed on Dec. 11, 2015.

(51) Int. Cl.

| | |
|---|---|
| *A61B 5/16* | (2006.01) |
| *A63H 3/00* | (2006.01) |
| *A63H 3/28* | (2006.01) |
| *A63H 33/00* | (2006.01) |
| *G16H 40/63* | (2018.01) |
| *G16H 50/20* | (2018.01) |

(52) U.S. Cl.
CPC ............ *A61B 5/165* (2013.01); *A61B 5/4082* (2013.01); *A61B 5/4088* (2013.01); *A61B 5/6892* (2013.01); *A61B 5/7275* (2013.01); *A61B 5/7405* (2013.01); *A61B 5/742* (2013.01); *A61B 5/7455* (2013.01); *A63H 3/006* (2013.01); *A63H 3/28* (2013.01); *A63H 33/006* (2013.01); *G16H 40/63* (2018.01); *G16H 50/20* (2018.01); *A61B 5/0002* (2013.01); *A61B 2503/04* (2013.01); *A61B 2562/0219* (2013.01); *A61B 2562/0247* (2013.01)

(56) References Cited

U.S. PATENT DOCUMENTS

| | | | |
|---|---|---|---|
| 2010/0020078 A1 | 1/2010 | Shpunt | |
| 2010/0118123 A1 | 5/2010 | Freedman et al. | |
| 2012/0015334 A1* | 1/2012 | Hamilton ........... | A63B 71/0622 |
| | | | 434/247 |
| 2012/0309592 A1* | 12/2012 | Myers ................. | A47D 13/063 |
| | | | 482/35 |
| 2013/0244533 A1* | 9/2013 | Elson ................... | A63H 33/006 |
| | | | 446/227 |
| 2016/0029962 A1* | 2/2016 | Hyde ................... | A61B 5/1171 |
| | | | 600/300 |

OTHER PUBLICATIONS

U.S. Appl. No. 15/376,072 (Abandoned) filed Dec. 12, 2016.
U.S. Appl. No. 14/012,466, filed Dec. 1, 2015 Issue Fee Payment.
U.S. Appl. No. 14/012,466, filed Sep. 22, 2015 Notice of Allowance.
U.S. Appl. No. 14/012,466, filed Sep. 9, 2015 Response to Non-Final Office Action.
U.S. Appl. No. 14/012,466, filed Jun. 9, 2015 Non-Final Office Action.
U.S. Appl. No. 15/376,072, filed Aug. 24, 2020 Notice of Abandonment.
U.S. Appl. No. 15/376,072, filed Nov. 18, 2019 Non-Final Office Action.
U.S. Appl. No. 15/376,072, filed Oct. 10, 2019 Response to Restriction Requirement.
U.S. Appl. No. 15/376,072, filed Jul. 2, 2019 Restriction Requirement.
Adde et al., "Computer Based Assessment of General Movements in Young Infants Using One Or Two Video Recordings," Pediatric Research, 70:295 (2011).
Adde et al., "Early prediction of cerebral palsy by computer-based video analysis of general movements: a feasibility study," Developmental Medicine & Child Neurology, 52:773-778 (2010).
Adde et al., "Identification of fidgety movements and prediction of CP by the use of computer-based video analysis is more accurate when based on two video recordings," Physiotherapy Theory and Practice, 29(6):469-475 (2013).
Adde et al., "Using computer-based video analysis in the study of fidgety movements," Early Human Development, 85:541-547 (2009).
Adde, L. "Prediction of cerebral palsy in young infants," Norwegian University of Science and Technology, Thesis, Apr. 2010.
Bregler et al., "Tracking people with Twists and Exponential Maps," Proceedings, 1998 IEEE Computer Society Conference on Computer Vision and Pattern Recognition, pp. 8-15 (1998).
Dusing et al., "Infants Born Preterm Exhibit Different Patterns of Center-of-Pressure Movement Than Infants Born at Full Term," Phys Ther. 89(12): 1354-1362 (2009) https://www.ncbi.nlm.nib.gov/pmc/articles/PMC2794478/.
Elgendi et al., "Real-Time Speed Detection of Hand Gesture using Kinect," Workshop on Autonomous Social Robots and Virtual Humans, the 25th Annual Conference on Computer Animation and Social Agents (CASA 2012), Singapore, May 2012.
Elgendi et al., "Towards arm tremor diagnosis," International Research Centre, Singapore National Research Foundation, Jul. 18, 2013.
Fan et al., "Augmenting Gesture Recognition with Erlang-Cox Models To Identify Neurological Disorders in Premature Babies," Proceedings of the 2012 ACM Conference on Ubiquitous Computing, 2012, pp. 411-420.
Gravem et al., "Assessment of Infant Movement With a Compact Wireless Accelerometer System," J. Med. Devices 6, 021013 (2012).
Hayes et al., "Supporting the Transition from Hospital to Home for Premature Infants Using Integrated Mobile Computing and Sensor Support," Personal and Ubiquitous Computing, 15:871-885 (2011).
Heinze et al., "Movement analysis by accelerometry of newborns and infants for the early detection of movement disorders due to infantile cerebral palsy," Med Biol Eng Comput 48:765-772 (2010).
McIntyre et al., "Cerebral Palsy - Don't Delay," Developmental Disabilities Research Reviews, 17:114-129 (2011).
Meinecke et al. "Movement analysis in the early detection of newborns at risk for developing spasticity due to infantile cerebral palsy," Human Movement Science 25:125-144 (2006).
Moody, "Approximate Entropy (ApEn)," https://www.physionet.org/physiotools/ApEn/ (Accessed on Mar. 15, 2017).
Park et al., "A Wearable Wireless Sensor Platform for Interactive Dance Performances," Fourth Annual IEEE International Conference on Pervasive Computing and Communications, Mar. 13-17, 2006, pp. 53-59.
Park et al., "Eco: An Ultra-Compact Low-Power Wireless Sensor Node For Real-Time Motion Monitoring," Proceedings of the Fourth International Symposium on Information Processing in Sensor Networks, Apr. 25-27, 2005, pp. 398-403.
Park et al., "Eco: Ultra-Wearable and Expandable Wireless Sensor Platform," 2006 International Workshop on Wearable and Implantable Body Sensor Networks (BSN 2006), Apr. 3-5, 2006, pp. 162-165.
Singh et al., "Involuntary Gesture Recognition for Predicting Cerebral Palsy in High-Risk Infants," Proc. ISWC, 2010, pp. 1-8.
Tsai et al., "EcoIMU: A Dual Triaxial-Accelerometer Inertial Measurement Unit for Wearable Applications," 2010 International Conference on Body Sensor Networks (BSN), Jun. 7-9, 2010, pp. 207-212.

\* cited by examiner 7, 8

5

8

Ecosystem Diagram

Baby 11: Elephant XY

ADVANCED PLAY ENVIRONMENT FOR SCREENING AND EARLY DIAGNOSIS OF INFANT DEVELOPMENTAL DELAYS AND NEUROLOGICAL IMPAIRMENTS

CROSS-REFERENCE TO RELATED APPLICATIONS

This application claims priority to U.S. Provisional Application Ser. No. 62/266,378, filed Dec. 11, 2015 and U.S. Non-Provisional application Ser. No. 15/376,072, filed Dec. 12, 2016, which are incorporated herein by reference in their entireties.

STATEMENT REGARDING FEDERALLY SPONSORED RESEARCH OR DEVELOPMENT

This invention was made with government support under NIH Grant Numbers 1R21HD084327-01 awarded by the National Institutes of Health. The government has certain rights in the invention.

FIELD OF THE INVENTION

The presently disclosed subject matter relates to a play environment for children and infants designed to evaluate neurological development and detect motor delays or impairments and provide an early warning for developmental disorders, and methods of using the same.

BACKGROUND

Developmental disabilities are becoming more prevalent in children in the United States. Each year, 1 in 40 children in the United States is born with an early motor delay, and 400,000 are born at-risk. According to the Center for Disease Control (CDC), about 1 in 323 children has cerebral palsy. Early detection of motor delays or impairments provides the opportunity for early treatment which improves health outcomes over the entire lifespan (McIntyre et al. 2011). Unfortunately, developmental disorders such as cerebral palsy have no biomarkers and therefore can only be diagnosed by observation.

Studies have shown that early intervention and rehabilitation (i.e., between the ages of 3 months and 11 months old) can provide the most effective results for children showing signs of motor delays and developmental disabilities, as the brain has plasticity at this age. Recognizing the importance of early detection, current national standards recommend that at-risk infants have a neuromotor exam at least two times during the first year of life (Spittle et al 2008). However, it is currently very difficult to diagnose developmental disorders in very young children (<11 months). Current screening tools for signs of developmental disorders vary in accuracy of diagnosis, and the predictive nature of these tests increases in accuracy with the age of the child. Successful early detection of delay or impairment in at-risk infants depends on the effectiveness of standard clinical scales, and many of those scales are not sufficiently sensitive to screen infants younger than 6 months (Leonard et al 2001). For example, one popular scale was reported to have a positive predictive value of 67% for motor or cognitive impairment at 1 year, i.e., high risk infants identified at 6 months using the screening tool were 67% more likely to have a motor and/or cognitive impairment at 12 months.

Some people have attempted to diagnose disorders in infants using motion capture system which are cumbersome, requiring the baby to sit in a special chair, wear markers for video motion capture, or wear accelerometers. Examples of such motion detecting systems are disclosed in U.S. Pat. No. 8,961,438 and U.S. application Ser. No. 14/012,466. Moreover, many current infant screening tools focus on qualitative assessments that are time consuming and vary in accuracy. Current and previous papers outlining studies utilizing sensorized toys for infant assessment do not allow for the infant to be in a natural play position (i.e., the subjects were seated upright in a high chair). Studies involving infant joint motion analysis use a variety of techniques, including complex Vicon 6 motion cameras and markers to assess infant and early childhood development. These tools and techniques are invasive and time-consuming, and do not provide reliable, quantitative results.

There exists a need, therefore, for a reliable tool to quantitatively, inexpensively, and non-invasively assess neuromotor development in infants, and specifically in infants under the age of 11 months old.

SUMMARY

The presently disclosed subject matter relates to a play environment for infants, which can be used to non-invasively evaluate infant neurological development and detect motor delays or impairments, as well as methods for using the same.

In certain embodiments, the present disclosure is directed to a play environment which comprises one or more toys equipped with sensors. In certain embodiments, the sensors are adapted for measuring at least one type of movement data. In certain embodiments the sensors are adapted for measuring at least one type of cognitive data. In certain embodiments, the sensor-equipped toys are placed above and/or around an infant to elicit responses such as, but not limited to touching, kicking, hitting, squeezing, reaching, or grasping. In certain embodiments, the toys are placed on the ground surrounding the infant. In certain embodiments, the toys are attached to bars or a framework such that the toys dangle above the infant. In certain embodiments, the sensor-equipped toys monitor and quantitatively measure such responses. In certain embodiments, the sensors collect and store the measurements in a database. In certain embodiments, the sensors collect and store the measurements in a microprocessor within the toy. In certain embodiments, the sensors collect and send data wirelessly from the toy to a central processor.

In certain embodiments, the present disclosure is directed to a play environment which comprises a mat, upon which the infant can be placed during the period of evaluation. In certain embodiments, the mat is equipped with sensors that are adapted for measuring at least one type of movement or cognitive data. In certain embodiments, the sensors collect and store data regarding the infant's movements in a database. In certain embodiments, sensor-equipped toys are placed peripherally around the infant on the mat.

In certain embodiments, the present disclosure is directed to a play environment which also comprises an eye-tracker to monitor the infant's gaze and reaction to visual stimuli.

In certain embodiments, the play environment contains one or more imaging sensors. The imaging sensors are adapted for measuring at least one type of movement data or cognitive data. In certain embodiments the imaging sensor can be any type of camera. Non-limiting examples of imaging sensors include a 3D Kinect imaging system and a stereo camera such as a GoPro.

In certain embodiments, the play environment contains one or more feedback mechanisms. The feedback mechanism generates a reaction in response to stimulus of one or more of the sensors. Non-limiting examples of reactions suitable for a feedback mechanism include generation of sound, vibration or light.

In certain embodiments, the present disclosure is directed to a play environment for evaluating neurological development in infants which comprises any combination or number of the one or more sensor-equipped toy(s), mat, eye-tracker described above, an imaging sensor and a feedback mechanism.

In certain embodiments, the present disclosure is directed to a method for evaluating neurological development in infants using any of the play environments described above. In certain embodiments, the play environment is used to detect motor delays or impairments. In certain embodiments, the data collected from the sensors in the play environment is analyzed and compared to other datasets to detect early signs of developmental disorders. In certain embodiments, the play environment is used to diagnose developmental disorder in a child or infant. In certain embodiments, the infant being evaluated is between the ages of 2 months and 11 months old.

In certain embodiments, the present disclosure is directed to methods for monitoring infant motion using any of the play environments above. In certain embodiments the method utilizes play environments comprising a mat. The mat can be equipped with sensors that are adapted for measuring at least one type of movement or cognitive data. The method includes the step of placing a child or infant into the play environment and measuring at least one type of movement or cognitive data. In certain embodiments, the movement or cognitive data is pressure or force data.

BRIEF DESCRIPTION OF THE FIGURES

FIG. 7. shows an example plot displaying how the elephant toy moved in the XY plane during a specific infant trial. The star marks the original position FIG. 8. shows a diagram illustrating how example mat data can be collected.

DETAILED DESCRIPTION

The present disclosure is directed to a play environment comprising sensor-equipped toys and/or a sensor-equipped mat to evaluate neurological development in infants, as well as methods of using the same in the early detection of developmental disorders or warning signs thereof.

A. Definitions

According to the present disclosure, a "child" is a human under the age of 18 years old. An "infant" is a child under the age of one-year old.

As used herein, the term "framework" refers to any structure which can be placed above or around an infant or small child, and to which toys or other objects can be attached.

B. Play Environment for Measuring Motor Responses

Figure 1:
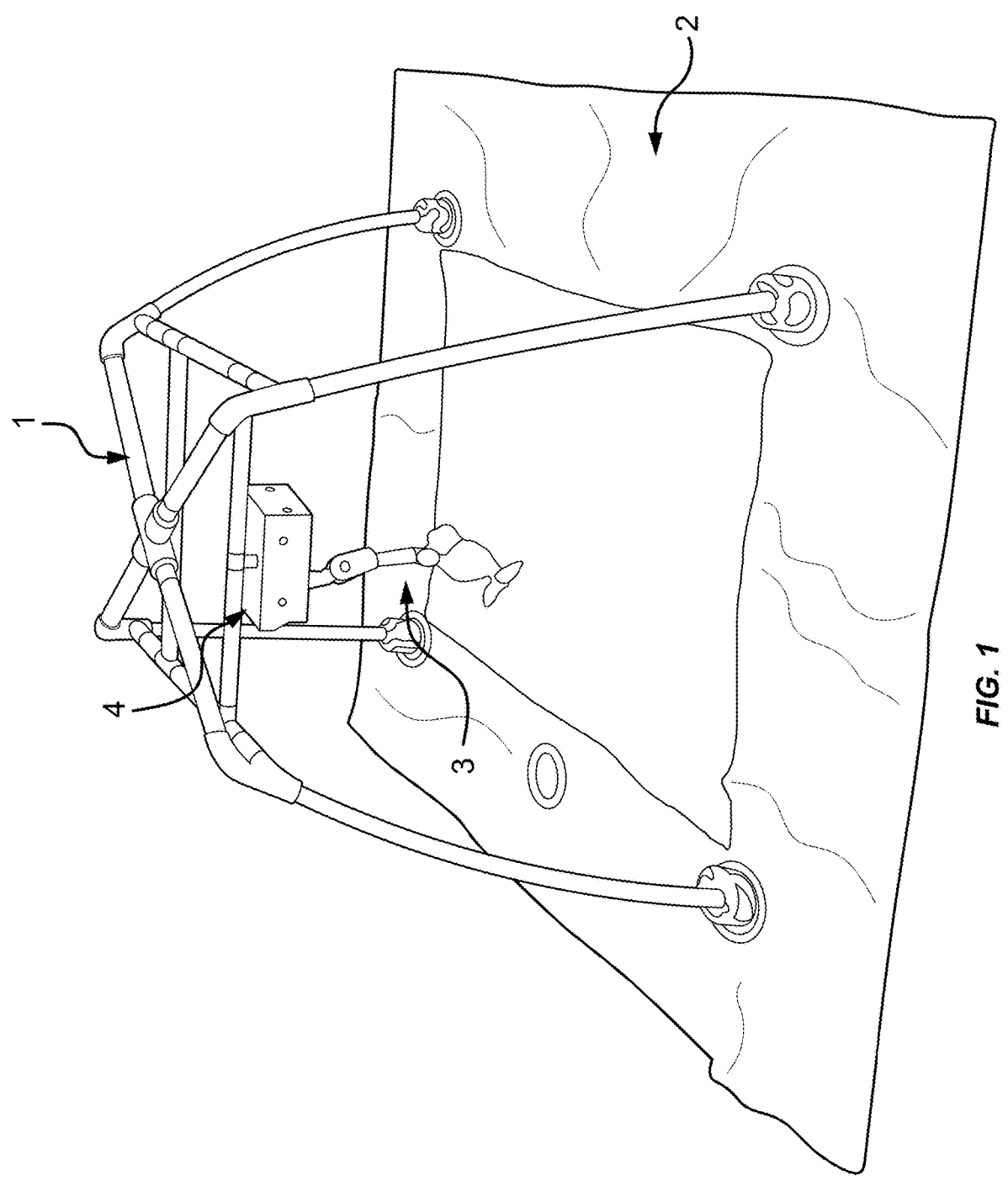
FIG. 1. shows an example play environment for observing and evaluating neurological development.
Figure 2A:
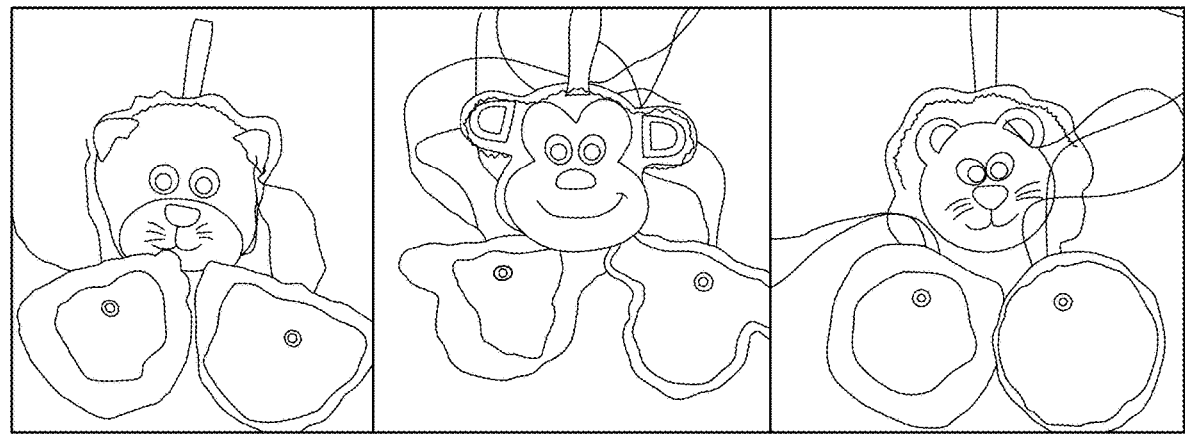
FIGS. 2A-2C. show example toys that are sensor-equipped.
Figure 2B:
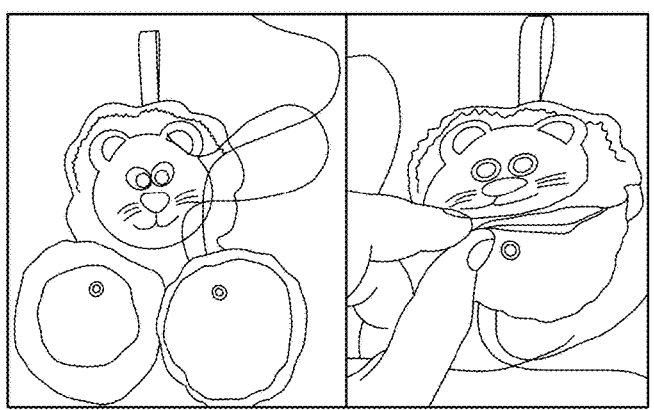
Figure 2C:
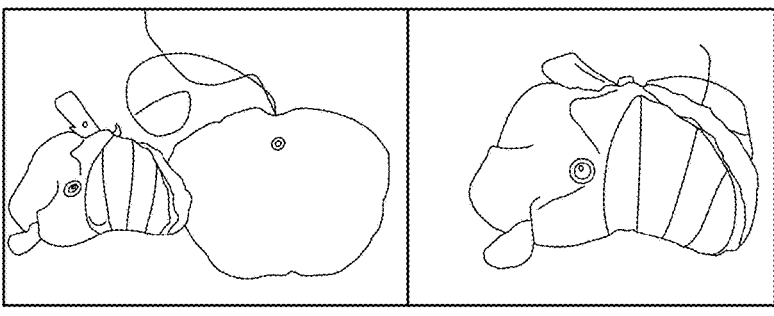
Figure 10A:
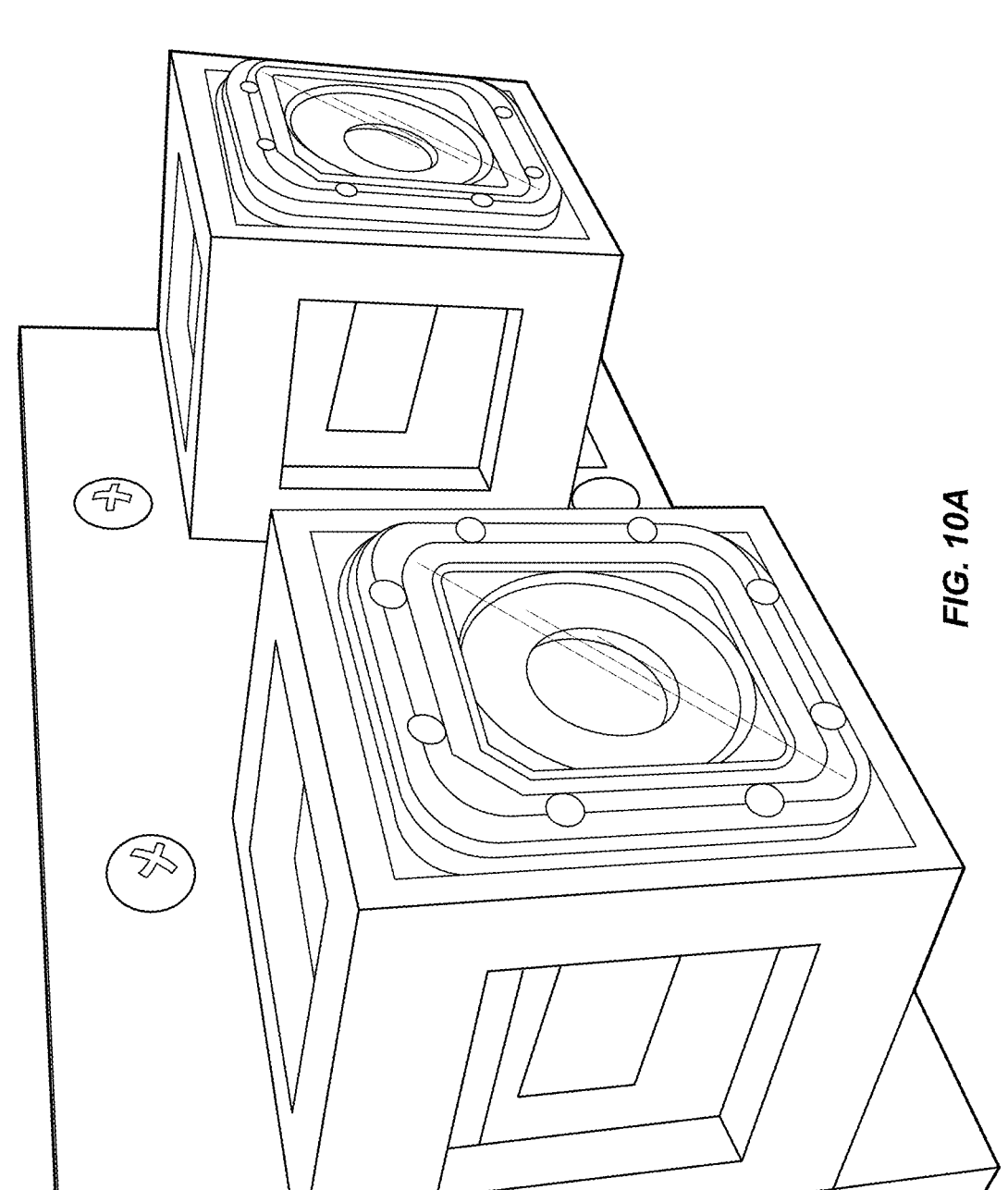
FIGS. 10. A-C. shows an example play environment utilizing multiple cameras.
Figure 10B:
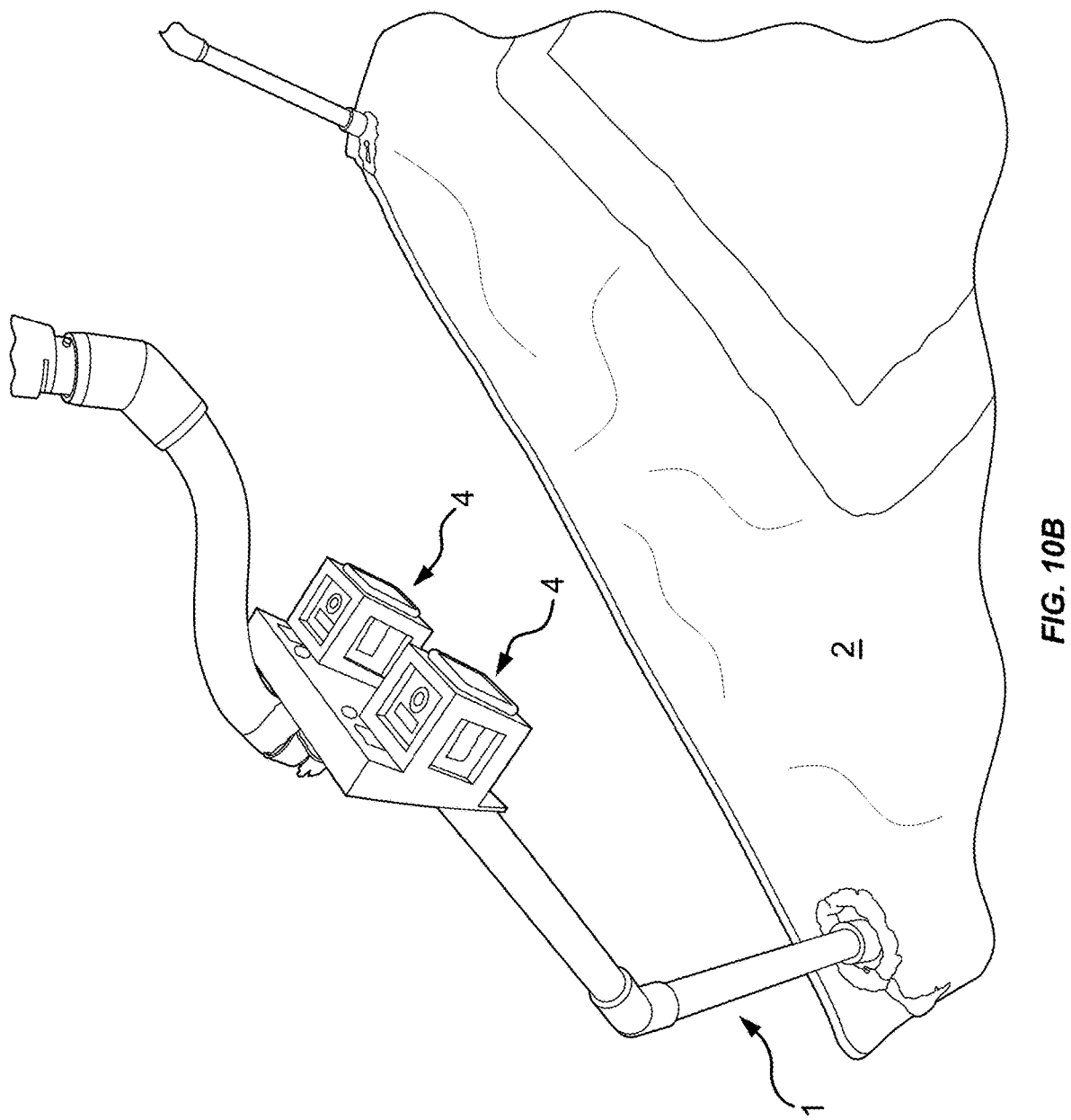
Figure 10C:
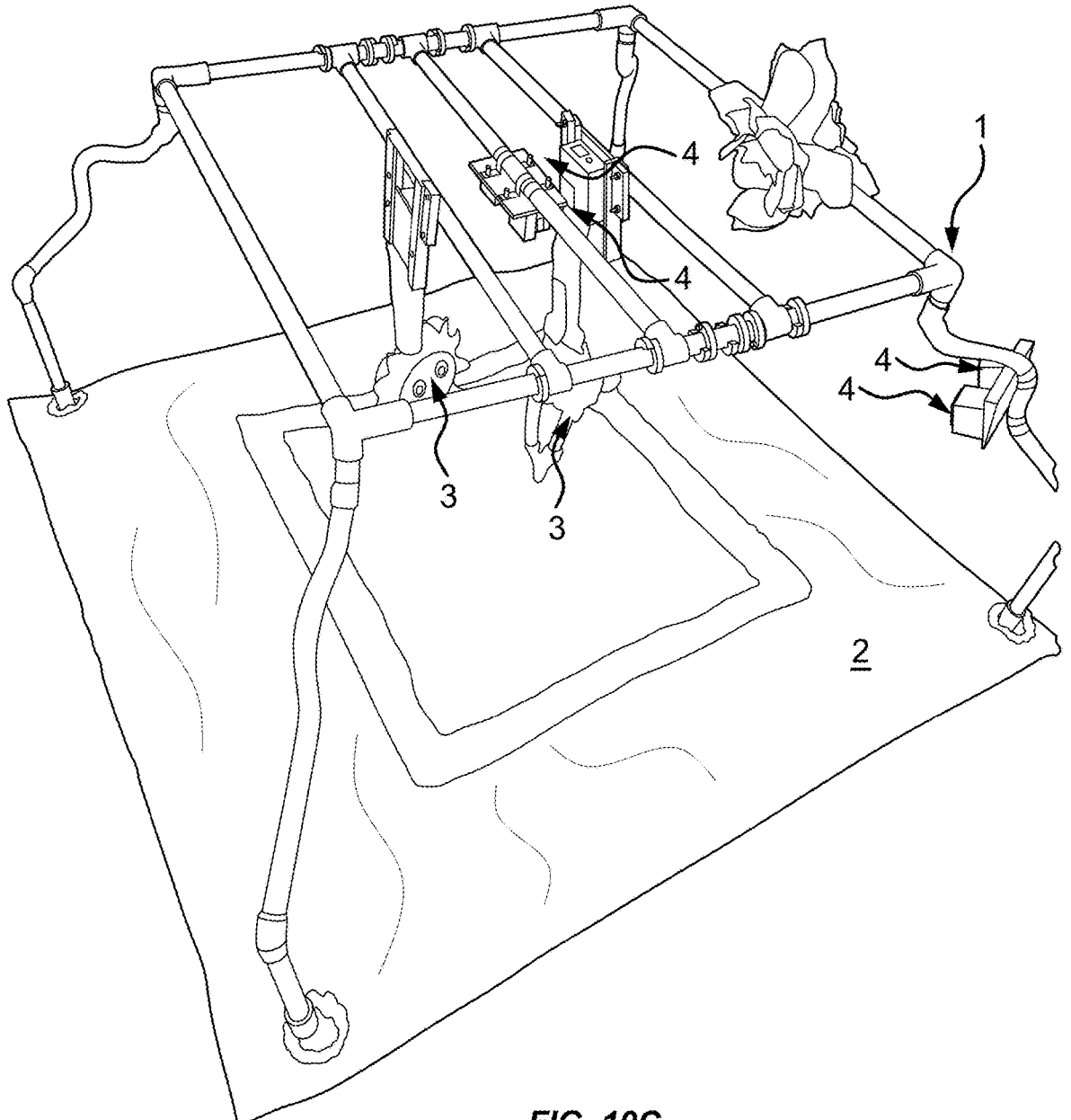

In certain embodiments, the present disclosure is directed to a play environment comprising one or more sensor-equipped toys (3), which can be used to measure motor responses in an infant or small child and to detect early signs of motor delay. The sensor-equipped toy can be any toy which is embedded with one or more sensors. In certain embodiments, the sensor can measure movement or cognitive data. In certain embodiments, the sensor can measure contact, touch, grasp, acceleration, toy position and/or orientation. In preferred embodiments, the sensor-equipped toys are age-appropriate and visually similar to common toys for infants and small children. In certain embodiments, the sensor-equipped toys are attached to a framework (1) comprising one or more bars, which may be made of flexible or inflexible material. The framework may be constructed using any materials and techniques used to build existing play environments. In certain embodiments, the play environment may be constructed from industrial parts and/or using a 3D printer. An example play environment framework (1) is depicted in FIG. 1. The framework (1) includes a cross connection to stabilize the structure and allow for easy break-down and portability, as well as adjustable parallel bars attached to the cross connection which can be used to hang toys above the infant. The surrounding mat area around the structure allows for the placement of peripheral toys that the child can interact with as they begin to develop motor skills. Sensor-equipped toys hang from the parallel bars within arm's reach of the infant, and within foot's reach of the infant while in the supine position. Another example play environment framework is depicted in FIG. 10C.

Sensors used in certain embodiments are adapted for measuring and/or collecting movement or cognitive data. Non-limiting types of movement data include: contact, touch, grasp, force, acceleration, velocity, orientation, position and pressure data. Movement data, for example, can include physical interactions. Certain physical interactions can be sub-divided into kinematic and haptic interactions. Non-limiting examples of kinematic interactions include: frequency of arm reach, frequency of leg kick, time to toy contact, toy movement, maximum toy displacement, or toy contact duration. Non-limiting examples of haptic interactions include: frequency of grasps or mean grasp force. In certain embodiments the sensors are adapted for measuring at least one type of cognitive data. Non-limiting types of cognitive data include attention, stimulus-response and play behavior data. Non-limiting examples of measuring cognitive data include measuring: frequency of toy stimulus event, frequency of toy feedback event, response time, frequency of touch response, frequency of look response.

In certain embodiments, the play environment comprises a framework with a "cross connection" or a "truss connection" designed to stabilize the structure and allow for easy break down and portability. Adjustable parallel bars may be attached to the framework to allow for the hanging of toys within arms' reach of the infant, and within foot's reach of the infant while in the supine position. In certain embodiments, the play environment also comprises a mat (2) which is placed below or around the framework. The surrounding mat area around the structure allows for the strategic placement of peripheral toys with which the infant or child can interact as they begin to develop motor skills. In certain embodiments, the mat is a pressure-tracking mat which is equipped with pressure sensors to detect movement.

In certain embodiments, the infant or small child is placed underneath and within the perimeter of the play environment. Alternatively, the play environment may be placed above and/or around an infant or small child such that the sensor-equipped toys are above and about the child to elicit responses such as touching, kicking, hitting, reaching, squeezing, or grasping.

In certain embodiments, the play environment further comprises an eye-tracker to monitor the baby's gaze and reaction to visual stimuli. In certain embodiments, sensor-equipped toys that make sounds may be used with the play environment to detect deafness as well as motor disorders.

Figure 3:
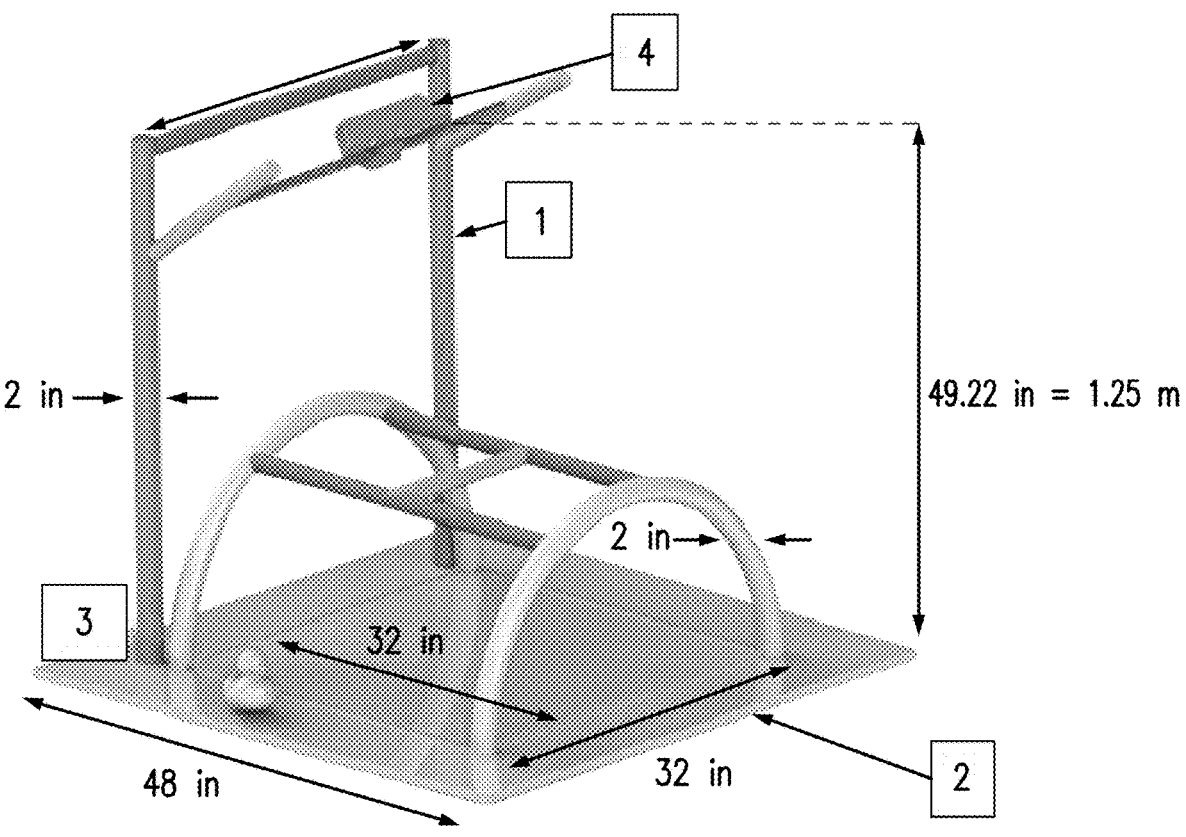
FIG. 3. shows an example play environment that includes a framework from which toys can be hung and imaging sensors can be attached.
Figure 5:
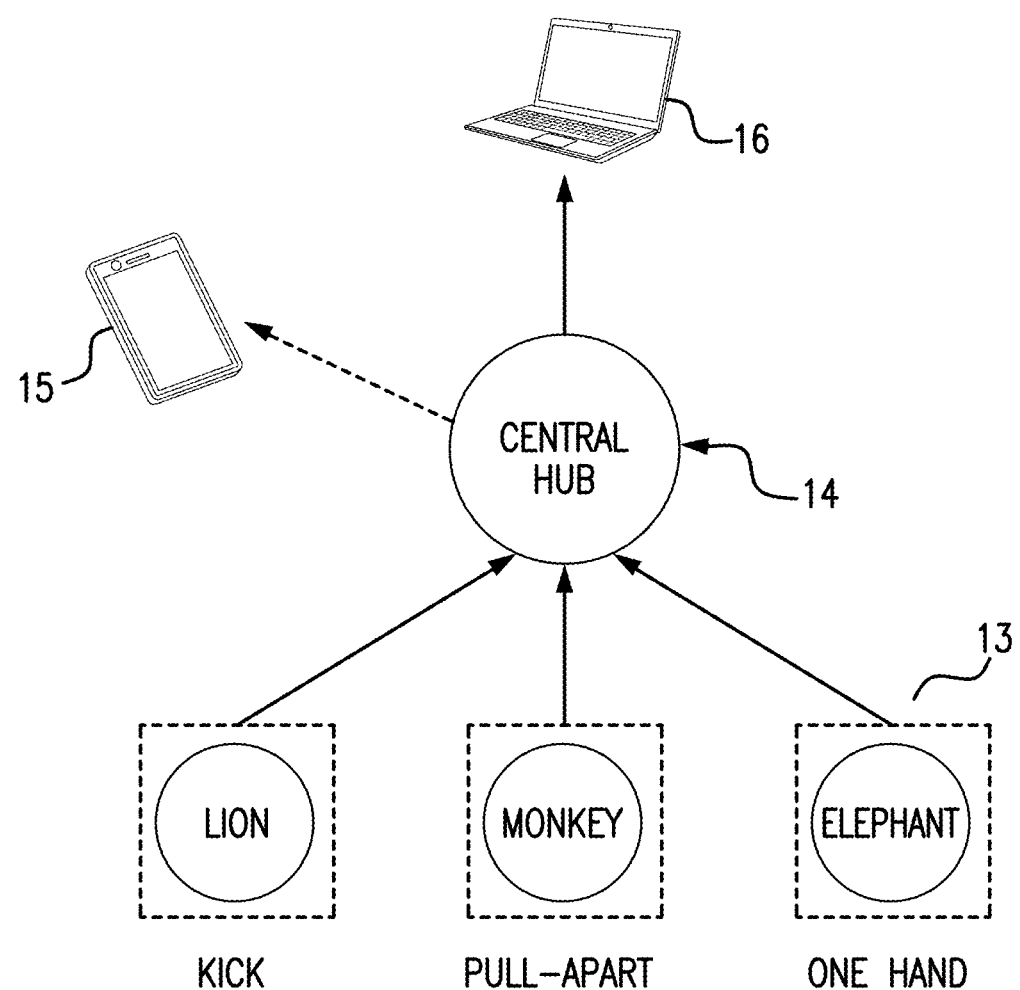
FIG. 5. shows an example system for data collection and information dissemination.

In certain embodiments, wireless data transmission can be integrated with the invention such that an infant's play session can be wirelessly transmitted to a pediatrician or other medical professional for analysis. Example embodiments are depicted in FIG. 5. Data is collected from sensors in the play environment (13) and transmitted to a central hub (14). From the central hub, the data is further transmitted to either or both of an activity app that can be monitored on a square feet and will accommodate toys at the periphery (FIG. 3, see duck). A pressure sensorized mat such as those made by Tekscan or Xsensor or a sensorized mat with four load cells at each corner placed under a 4 ft×4 ft dragon plate will be placed between a blanket and the base of the gym; this mat will be used to measure postural changes to detect rolling, crawling and other movements away from the initial posture—reasonable specifications would be sensor density 0.25-1 sensor/cm$^2$ with a spatial resolution about 1 cm$^2$, adapted for measuring vertical reaction forces up to 120 Newton (Donati 2013). In certain embodiments, an imaging sensor may be used, such as a 3D motion capture system. In certain embodiments, the 3D motion capture system will include stereo cameras mounted to the framework structure to enable collect video data and the infants' reaching and body kinematics in response to the toys. In certain embodiments, a 3D Kinect camera may be used as the motion capture system and if used, the Kinect camera will be mounted at least 1.2 m to get good resolution.

In certain embodiments, a computer will collect data from the wireless sensor network (WSN) via one or more microprocessor as well as the data from the pressure mat and the camera. In certain embodiments, a wireless chip such as Xbee can be used in connection with the toy-based platform; this chip can communicate with a microprocessor via another wireless unit located off the gym. In certain embodiments, data can be temporally synchronized using a digital pulse generated by a go-button and spatially synchronized to the inertial frame of the camera location. In certain embodiments, a visual parsing and tracking program can analyze the sensor data including the camera data; e.g., to detect the infant torso, each hand and foot of the infant and extract position over time.

TABLE 1

| Examples of Toys to be used. | | | | |
|---|---|---|---|---|
| Hanging Toys | Toy location | Action-Stimulus *light or sound will be reward | Infant Posture | Target Age |
| 1. Toy animal for leg reach (Lion) (FIG. 4C) | At feet | Shake, Sound/Music | Supine, Seated | 2-5 |
| 2. Ring Toy: soft or hard | Side or Center | Grasp, Shake, Squeeze | Supine, Seated | 3-5 |
| 3. Plush Elephanttoy (FIG. 4A) | Side or Center | Squeeze Tips and nose | Supine, Seated | 3-5 |
| 4. Organtan (two part toy) (FIG. 4B) | Side or Center | Pull apart/put together | Supine, Seated | 7-10+ |
| Peripheral Toys | | Action-Stimulus | Target Posture | Target Age |
| 1. Monkey Toy (FIG. 4D) | Outer 1 | Grasp, Hit | Seated, Crawl | 8-10+ |
| 2. Tree Toy (FIG. 4E) | Outer 2 | Grasp, Squeeze | Seated, Crawl | 8-10+ |
| 3. ball | Outer 3 | Grasp, Roll, Shake | Seated, Crawl | 8-10+ |
| 4. Alligator toy (FIG. 4F) | Outer 4 | Grasp, Squeeze | Seated, Crawl | 8-10+ | cell phone or other device to be accessed by a parent (15) or to a computer to be accessed by a physician (16).

In certain embodiments structure of the proposed system will have a framework, sufficiently sturdy to accommodate infants of different sizes, to allow an adjustable mount for cameras and to allow adjustable mounting for hanging toys (see H bar, FIG. 3 and FIG. 10C). In certain embodiments the square footage will be about 9 square feet to about 16

In certain embodiments these toys will be modified commercial toys. In certain embodiments these toys will be custom-made toys. In certain embodiments, each toy can have a unique identifier so that its position will be known with respect to a designated inertial frame. In certain embodiments, each toy can be sensorized appropriately. Toys can be equipped with one or more pressure and force sensors to detect some level of infant grasping forces from gross and fine motor manipulation. In certain embodiments, inertial sensing units ("IMU") (gyroscope, accelerometers, and magnetometer) can be used to detect twisting, turning, shaking, actions experienced by the toy. In certain embodiments, the toys provide feedback, such a sound, vibration or light, depending on whether the infant grasps, shakes or touches it. In certain embodiments, and for safety, short tethers can be used with the toys to allow handling of the toy without loss during handling. In certain embodiments, the outer parts of toys can be washable or wipeable. In certain embodiments, electronics can be removable from the outer part to enable ease of washing. In certain embodiments, toys should enable grasping of a key part.

Figure 4A:
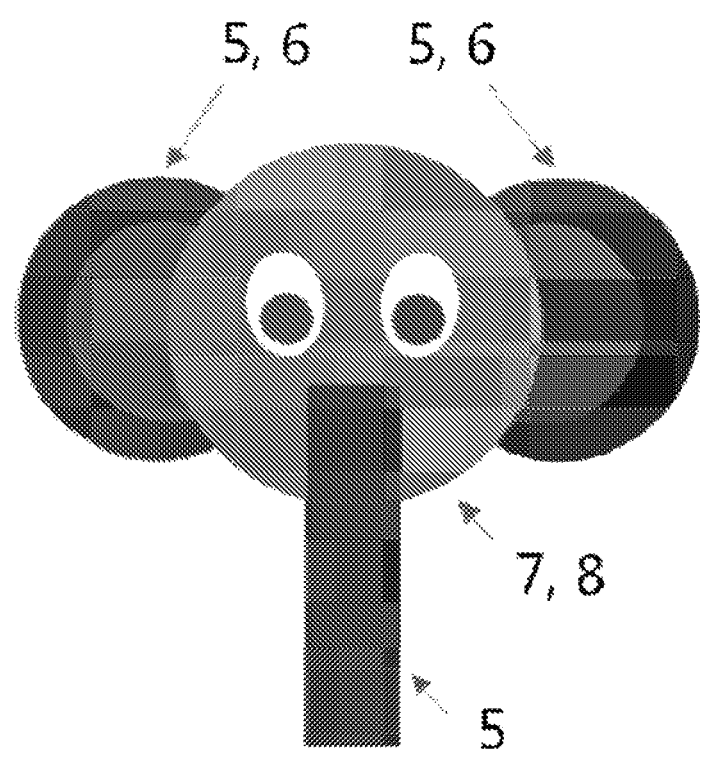
FIGS. 4A-4F show example toys that can be utilized in the play environments or the methods of the disclosed inventions are depicted. Example sensors and feedback mechanisms that can be included in toys are illustrated.

Examples of toys with that can be used in play environments are depicted in FIGS. 2A-2C and 4A-F. In FIG. 4A, the example toy, which is an elephant, has a pressure sensor (5) and a feedback mechanism, which produces vibration (6) in each ear. The elephant toy also has a pressure sensor embedded in its trunk and an IMU (7) as well as a feedback mechanism that produces sound (8) in the elephant's head.

Figure 4B:
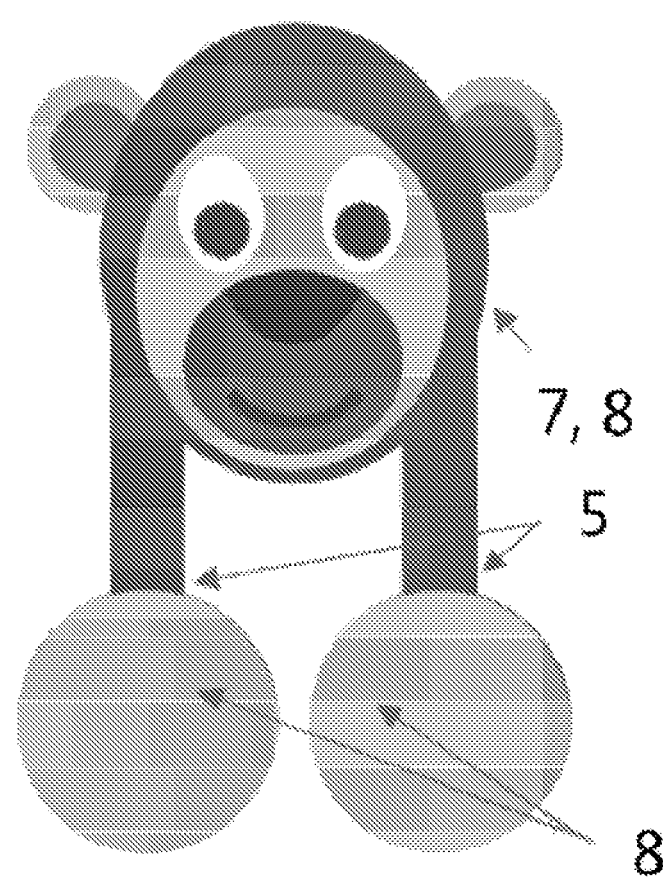

In FIG. 4B, the example toy, which is an orangutan, has two pressure sensors (5) embedded in each arm. The arms are attached to a feedback mechanism that produces sound (8) when the arms are apart and separated. The orangutan toy also has an IMU (7) as well as a feedback mechanism that produces sound (8) in the orangutan's head.

Figure 4C:
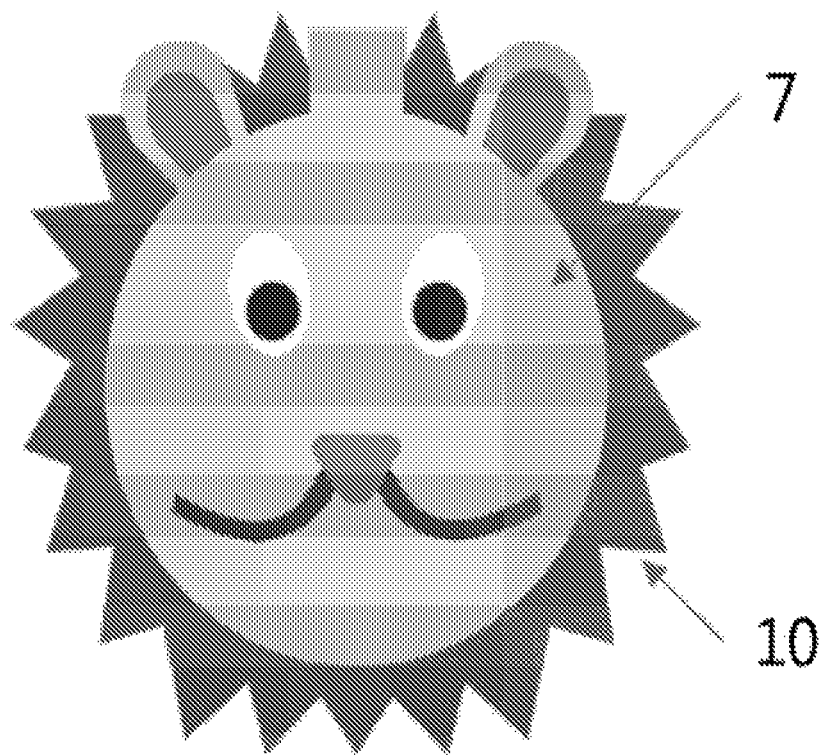
Figure 4D:
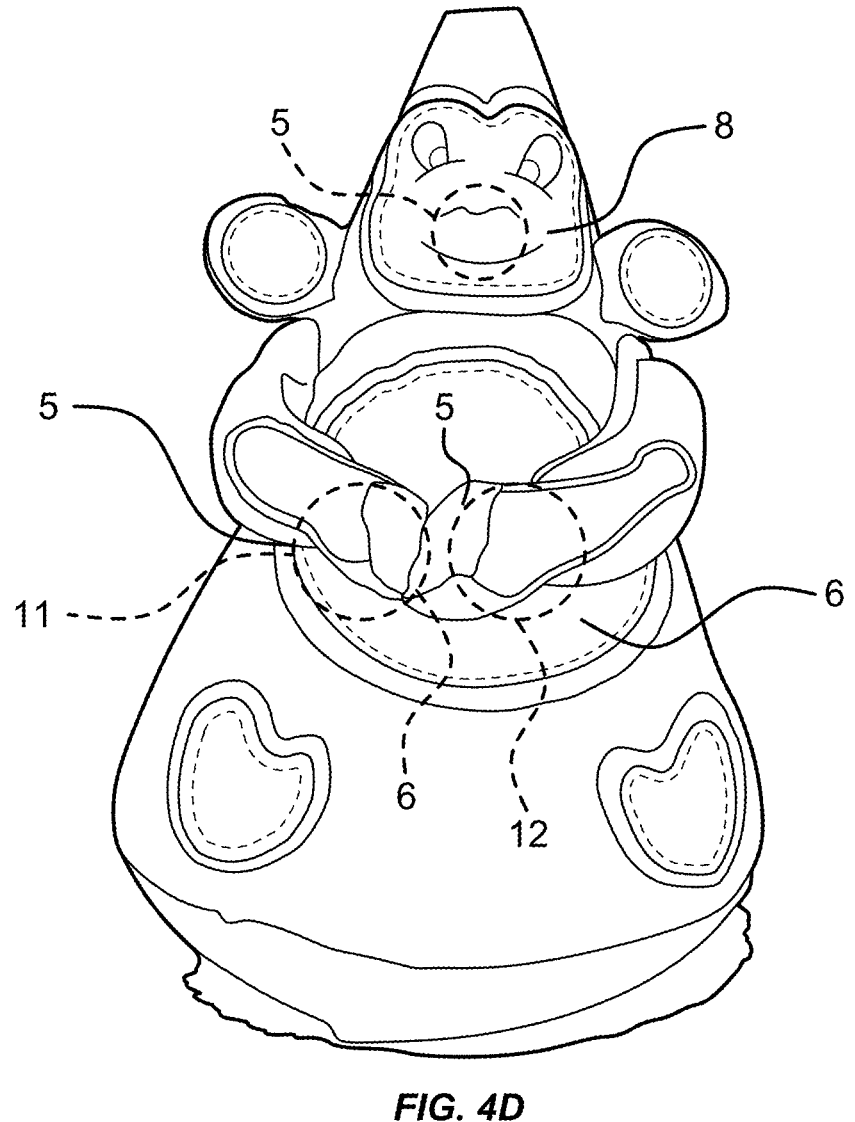

In FIG. 4C, the example toy, which is a lion, has an IMU (7) and a feedback mechanism that produces light (10) in the lion's head In FIG. 4D, the example toy, which is a monkey, has embedded pressure sensors (5), feedback mechanisms that produce vibration (6) and sound (8), and magnets in the arms (12) that are attached to a reed switch (11).

Figure 4E:
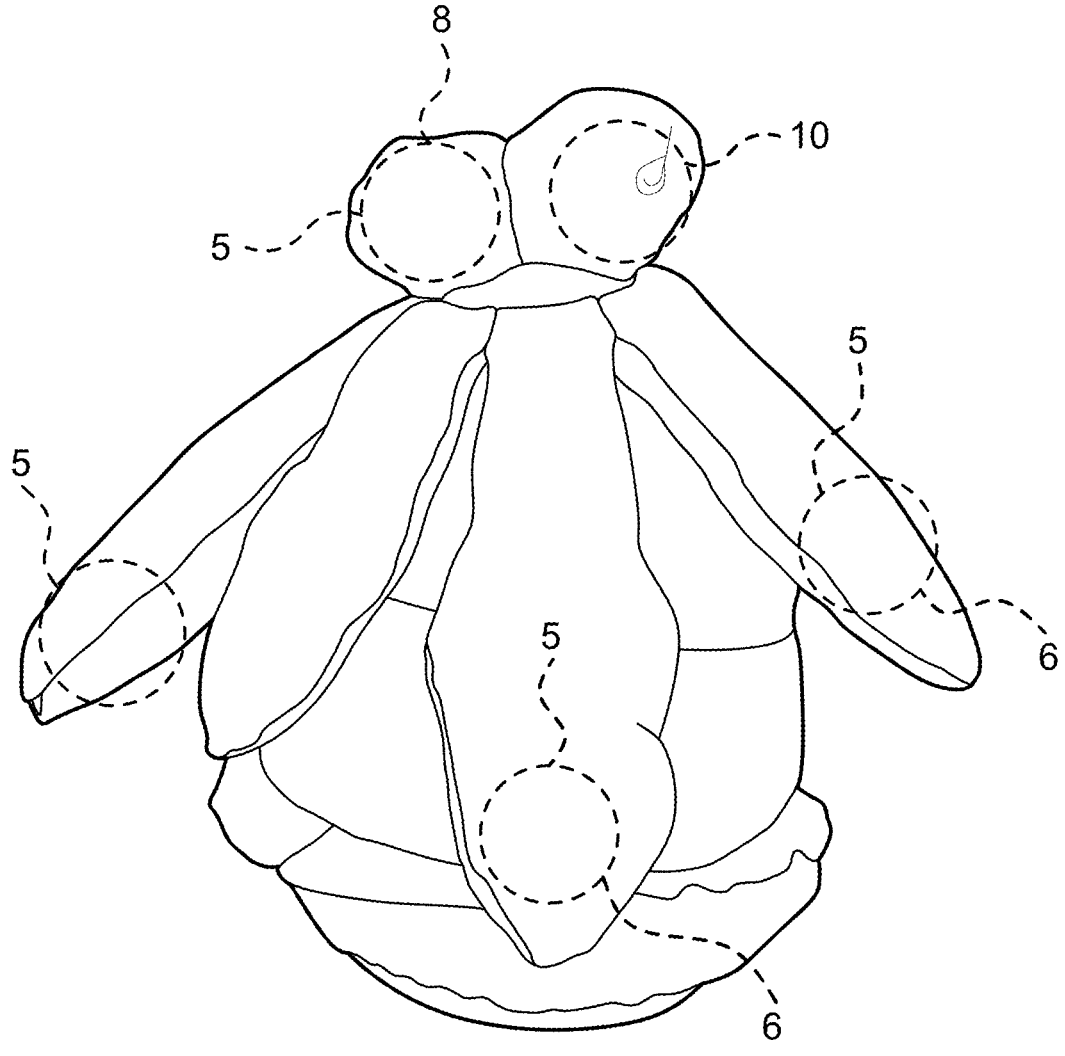

In FIG. 4E, the example toy, which is a tree, has embedded pressure sensors (5) and feedback mechanisms that produce vibration (6), sound (8), and light (10).

Figure 4F:
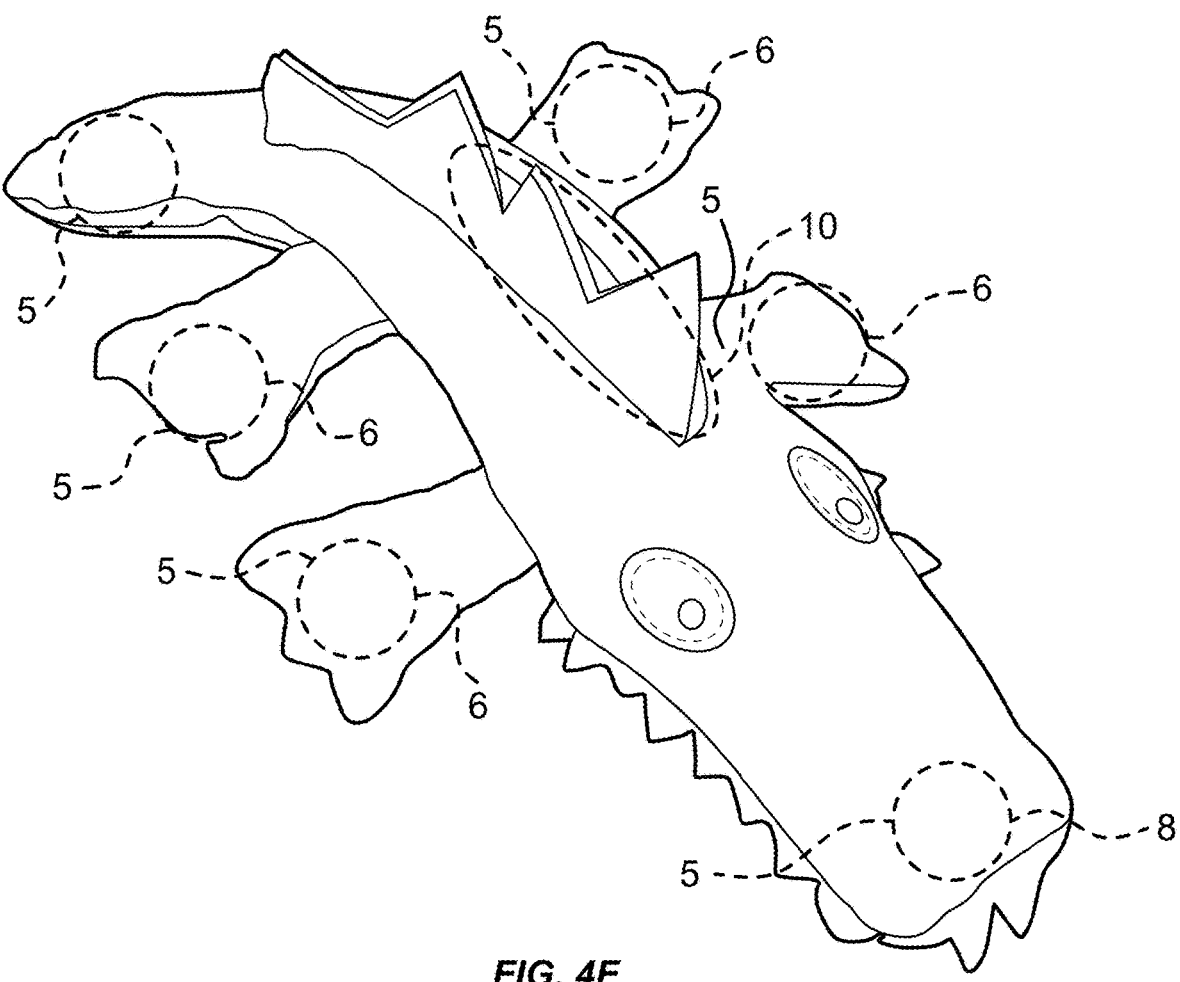

In FIG. 4F, the example toy, which is a crocodile, has embedded pressure sensors (5) and feedback mechanisms that produce vibration (6), sound (8), and light (10).

TOYS FOR YOUNGER INFANTS (2 months-7 months). In certain embodiments, toys above head can be accessible to the baby supine or seated and toys placed at the periphery can be accessible to the crawling baby. In certain embodiments, five toys can be hanging (1 at each foot, 1 over left side, 1 over right side, 1 center) (Table 1). In certain embodiments, and to identify reaching behaviors with the feet, a toy can be hung by the left and right foot of the infant. In certain embodiments, the toy can provide sound when the infant kicks it. To identify reach and/or grasp behaviors with the left hand, right hand or both, toys can be hung to the center, right, and left of the baby. Kicking behaviors should be evident at 2 months. Reaching and gross grasping behaviors should be evident starting at 3 months and finer motor grasping should be evident at about 4 months (Ho 2010). In certain embodiments, and to identify any differentiated bimanual actions where the right and left arm has different roles in a bimanual task, one toy can be a two part toy that the infant can put it together or take it apart. This insert and remove behavior should be very evident starting at 7 months (Kimmerle 2010). In certain embodiments, the toy can provide feedback, such as sound, vibration or light for the removal or insertion action. In certain embodiments, the other toys can be single part toys that cannot come apart such as a ring toy.

TOYS for OLDER INFANTS (7 months-10+ months). In certain embodiments, and to identify intentional crawl and roll movements toward a toy, three toys can be placed on the periphery to engage the infants who begin to crawl (Ho 2010). These toys should encourage baby to "go" after them—but they should not move to far away e.g., a hit, a squeeze causes a movement—crawling, rolling etc. but doesn't move too far away; and encourages baby to repeat action.

C. Methods for Evaluating Neurological Responses and Detecting Developmental Disorders In certain embodiments, the present disclosure is directed to a method of evaluating neurological development using the play environments of the present disclosure.

In certain embodiments, the present disclosure is directed to a method of diagnosing a developmental disorder using the data collected from the use of the play environments of the present disclosure.

In certain embodiments, the play environments can be used by hospitals and private pediatrician practices. In other embodiments, parents can buy or rent the play environments of the present disclosure from their hospital or pediatrician, and use it for evaluation at home. The play environment of the present disclosure can also be deployed to remote areas, including third world countries.

TABLE 2

| Primary and Secondary Measures (*collected daily for 5 days): Y = Young (3-5 months) | | | | |
| --- | --- | --- | --- | --- |
| Variable Construct | Ex. Measure | Measure Ref. | Sample Item(s) | Ex. Averages (STD) |
| Unimanual (L, R) and Bimanual Arm use (B, D-B) | % Frequency | Sgandurra 2012 Corbetta 2008 Kimmerle 2010 | % grasping actions % reaching actions | % freq grasp to center toy: TYPICAL: L; Y: 16.67(4.16)%; 0: 35(7.26)% |
| Leg Use (L, R) | % Frequency | — | % kicking actions to elicit stimuli | — |
| Grasp Forces | Mean Force or Pressure | Cecchi 2011 Guzetta 2014 Sgandurra 2012 | Magnitude of squeezing or pinching action | TYP: L (Newtons) Y: 8.07 N, 0: 12.32 N |
| Arm Use: Position | Mean Distance | Bhat 2006 | Distance of each wrist to toy | R distance to toy: TYP Y: 250 mm, 0: 185 mm |
| Arm use: Speed | Mean Speed | Bhat 2006 | Mean hand speed from baseline | R speed to toy: TYPY: 170 mm/s; 0: 220 mm/s |

EXAMPLES

The following examples are put forth so as to provide those of ordinary skill in the art with a complete disclosure and description of how to make and use the presently disclosed subject matter, including the use of the play environments of the present disclosure to measure motor responses and evaluate neurological development. The following examples are not intended to limit the scope of what the inventors regard as their presently disclosed subject matter. It is understood that various other embodiments may be practiced, given the general description provided above.

Example 1

FIG. 1 depicts a prototype of a play environment of the present disclosure, called a SmarToyGym. The play envi-

Example 2: SmarToyGym

A study was performed to quantify the physical and cognitive interactions of low-risk and high-risk infants in a sensorized play environment in a cross-sectional study to investigate whether there are differences between the two groups, and if these differences are indicative of possible motor delays and impairments. A goal is that the results from this study can highlight the specific metrics that are important to focus on when separating the low-risk and at-risk infants.

To analyze the data, two different types of metrics are measured: physical and cognitive infant interactions with the toys. Physical interactions can be split up into two subcategories: kinematic and haptic interactions. Table 2 consolidates and displays the wide range of variables that can be collected.

TABLE 2

Variables analyzed in the SmarToyGym project.

| Type of Interaction | Variable | Description |
|---|---|---|
| Kinematic | Frequency of arm reach | The number of reaches, split into left, right, and bimanual reaches |
| | Frequency ofleg kick | The number of kicks, split into left, right, and bimanual kicks |
| | Time to toy contact (s) | Time in seconds of first infant-toy contact |
| | Maximum toy displacement | The maximum displacement in the XYZ direction |
| | Toy contact duration (s) | Time in seconds of infant interaction with toy |
| Haptic | Frequency of grasps | The number of grasps, split into left, right, and bimanual grasping |
| | Mean grasp force (psi) | Grip force in psi |
| Cognitive | Frequency of toy stimulus event | Frequency of events to prompt the infant's attention |
| | Frequency oftoy feedback event | Frequency of key toy events triggered after infant interaction |
| | Response times (s) | Time in seconds of infant's response to events |
| | Frequency of touch response | The number of times the infant touched the toy after an event if previously not engaged |
| | Frequency of look response | The number of times the infant looked at the toy after an event if previously not engaged | ronment visually appears similar to existing toys for infants. Sensor-equipped toys dangle down in front of the child, while the baby's movements are captured using a Microsoft Kinect Sensor and a mat equipped with pressure sensors. The framework for the play environment was built using industrial parts and a 3D printer. A 3D Kinect imaging system is currently embedded into the prototype and software has been developed. The Kinect can be a component of the advanced play environment and it can discriminate kinematic movements of atypical vs. typical infants in response to the presence of a toy. These toys can be networked and embedded with sensors to measure touch, grasp, acceleration, toy position and orientation. They can provide light and sound stimuli and the infant's head turning, leg kicking, hand touch and grasp responses can be collected by the embedded processor and analyzed by a custom GUI (this may be on a PC or via an app). The data from the child's movements can be compared with past datasets (for example, the previously past data sets compiled in Table 2) to provide an early warning of developmental disorders, and datasets can be built for identifying problems. The device is not specific to any one disorder, for example, toys that make a sound could be used to detect deafness as well as motor disorders.

FIG. 10C depicts another version prototype of the play environment of the present disclosure where 3D stereo cameras are used instead of the Kinect camera.

Two sensors are positioned inside the toys: an IMU and a pressure sensor. Each toy is rigidly connected to an electronic box and is able to rotate about the XYZ axes about one fixed point. To quantify toy displacement, a robotic model based on Denavit-Hartenberg parameters was used. The robotic model used is similar to a rigid pendulum suspended from a spherical joint with 3 degrees of freedom (revolute joints). A zero reference frame was set in the system to graphically display toy movement based on these calculated displacements. Image data analysis confirmed these variables.

Figure 6:
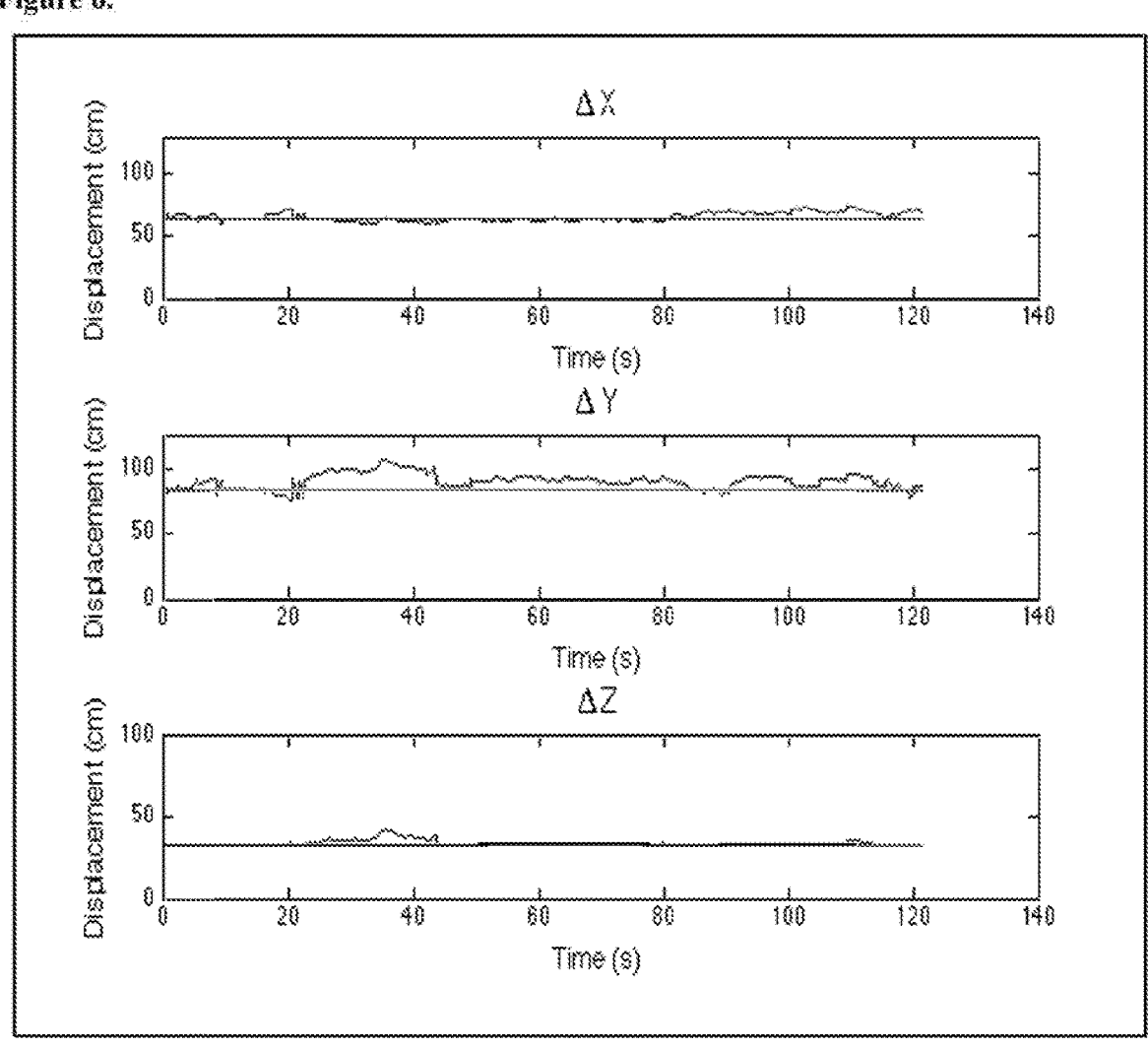
FIG. 6. shows representative data displaying the X, Y and Z displacement of the elephant toy during a specific infant trial.
Figure 7:
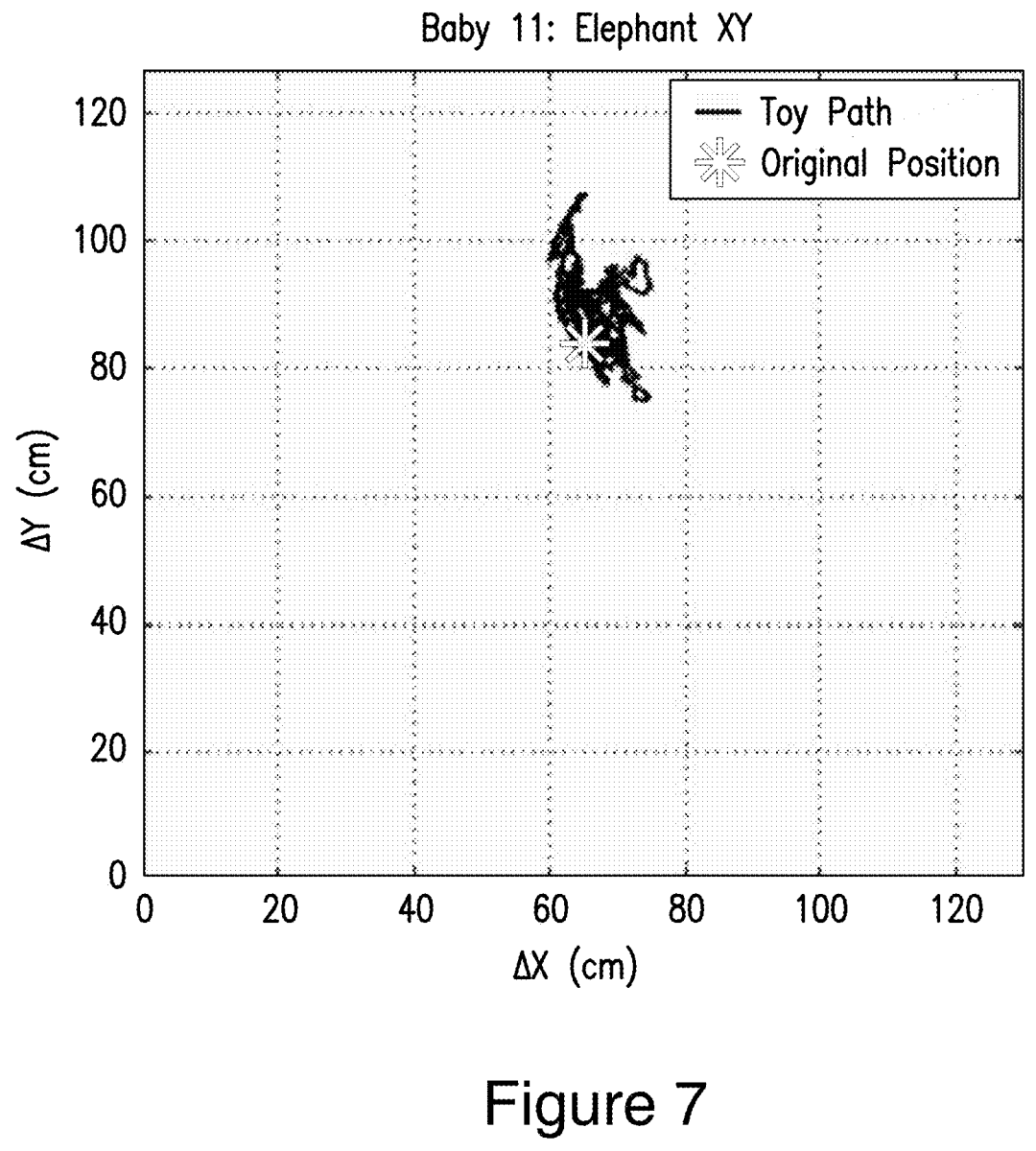

From this study, representative data displaying XYZ displacement of the elephant toy during a specific infant trial is shown in FIGS. 6 and 7. FIG. 6 depicts the displacement of the toy in the X, Y, and Z directions on separate 2D plots. FIG. 7 shows the XY displacement in a single 2D plot, with a star denoting the toy's starting position. In the depicted example, the infant moved the toy at a maximum displacement of x=9.9 cm, y=23.5 cm, and z=10.3 cm.

Example 3: SmarToy Vision System

A play environment was developed with imaging sensors, referred to herein as the SmarToy Vision System. This involved developing a imaging system that would allow for multiple view 3D tracking of the infant under natural play conditions. A stereoscopic imaging framework that can support off the shelf camera devices, such as a GoPro or Kinect, but still generate accurate depth maps, can be utilized. The example SmarToy Vision System depicted in FIG. 10 utilizes 4 GoPro stereo cameras (4). The cameras in the example system are attached to the framework (1) and aimed at the mat (2) as depicted in FIGS. 10B and 10C.

Given the size constraints of the play environment of the present example, a 3D stereo camera framework was employed over depth cameras such as the Kinect because of the ability to manually specify the stereo baseline to accommodate depth estimation of nearby objects. To become robust to interaction based occlusion a dual stereo camera setup can be used (as depicted in FIG. 10A) with each setup positioned almost orthogonally to each other (as depicted in FIG. 10C). This allows the play environment to track the infant from almost complementary viewpoints, giving it the ability to view the infant's limbs at any given point of time free of severe occlusion.

Example 4: Mat Data

Figure 8:
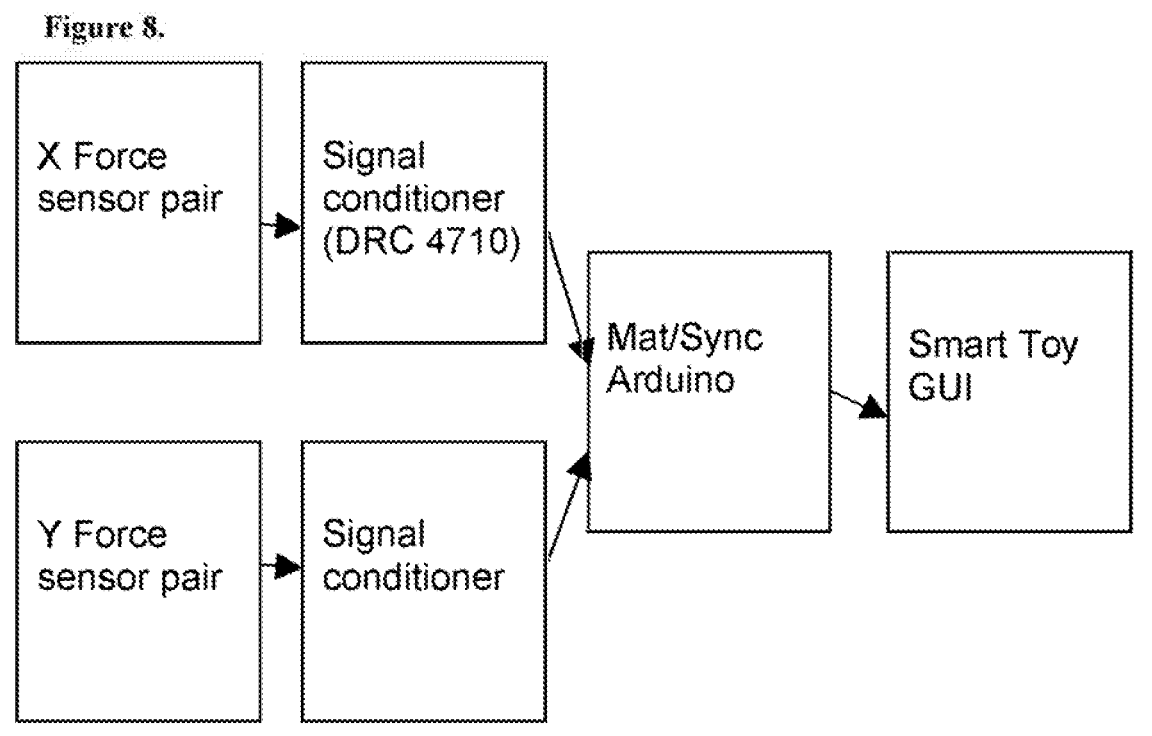

In this example, data was collected from a play environment which had sensors embedded in a mat. The raw mat data is collected in the way depicted in FIG. 8. The force sensor data collected from each corner of the mat is resolved into center of pressure data as shown in this figure. Each "x" denotes the babies center of pressure from the beginning of the trial to the end of the trial. This information indicates how the infant moved.

Figure 9:
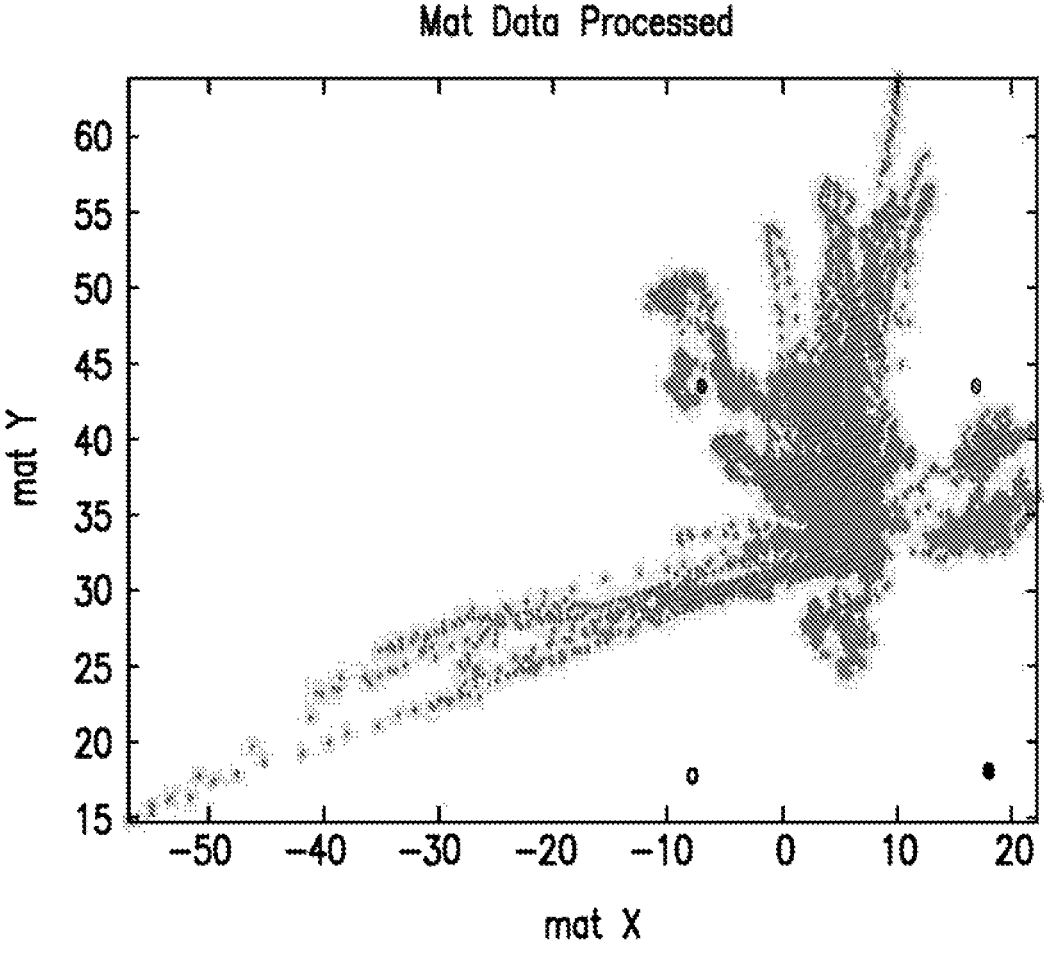
FIG. 9. shows a plot of example mat position data.

This raw data, centered around 280 with a span of 560 units (roughly 1.8-3.6V converted to analog), is saved by the GUI into a .txt file. This file is then processed by the matlab script SmarToyMATpostProcessing_vl.m, which takes the data and performs a linear mapping to x,y coordinates −24 to 24" along each dimension. The red corner (bottom left when viewed from above) is −24, 24, and the blue corner (top right) is 24,24. Alongside the raw data, calibrations are taken before each trial by placing a known mass in each mat corner and then in the center to ensure consistency across data sets. This is factored into the post-processing script to determine corner values and locations. The output of this script is an array of position data and a plot of baby motion on the mat, as can be seen in FIG. 9.

Processing can occur via a standard Matlab script, which focuses on the y-axis motion, also known as caudal-cephalic motion (along the axis of the spine). Center-of-pressure ("COP") movement along this axis has been found to be distinct between healthy and non-healthy infants (https://www.ncbi.nlm.nih.gov/pmc/articles/PMC2794478/ which uses preterm vs. full term infants). The script can measure root mean square ("RMS") displacement and approximate entropy (ApEn) along the y-axis. Larger RMS and a smaller ApEn is expected in healthy infants. RMS can be measured as the sum of deviations from the mean COP. ApEn is a measurement of the predictability of a data set, and is significantly more complicated in its calculation. It is used commonly in measuring repetitive biological signals such as EKG, as well as motion data. An overview is found at https://www.physionet.org/physiotools/ApEn/ and the aforementioned paper gives a number of evaluation constants which would also be applicable to the present data set.

Overall, the analysis can confirm the occurrence different events based on the play environment data collected, including vision-based baby tracking (Center of Pressure and limb tracking) and mat pressure (Center of Pressure).

What is claimed is:

1. A play environment for evaluating neurological development and diagnosing a developmental disorder in a child comprising:
   a. a mat;
   b. one or more toys comprising an IMU sensor and a pressure sensor, wherein the one or more toys are placed in proximity to the child; and
   c. an imaging sensor configured for tracking the child while interacting with the one or more toys;
   wherein the IMU sensor, the pressure sensor, and the imaging sensor, are each communicatively coupled to a central processor, and configured to collect and send at least one type of movement data and cognitive data to the central processor, wherein said movement data comprises physical interactions including kinematic and haptic interactions, or said cognitive data comprises a variable selected from the group consisting of frequency of toy stimulus event, frequency of toy feedback event, response times, frequency of touch response, and frequency of look response, and wherein said movement and cognitive data is compared with a past dataset to identify warning signs of a developmental disorder.

2. The play environment of claim 1, wherein said one or more toys are adapted for collecting and measuring at least one type of movement data or cognitive data.

3. The play environment of claim 2, wherein said one or more toys further comprises a feedback mechanism that generates sound, vibration or light.

4. The play environment of claim 1, wherein said mat is embedded with one or more sensors, said one or more sensors are adapted for collecting and measuring at least one type of movement data or cognitive data.

5. The play environment of claim 1, further comprising a framework.

6. The play environment of claim 5, wherein said framework comprises a cross connection, wherein said cross connection comprises two to four flexible bars.

7. The play environment of claim 5, wherein said framework is collapsible.

8. The play environment of claim 6, wherein said framework further comprises one or more adjustable parallel bars attached to the flexible bars of the cross connection, wherein said parallel bars are detachable from the flexible bars.

9. The play environment of claim 5, wherein said one or more toys are attached to said framework.

10. The play environment of claim 1, wherein said imaging sensor comprises a motion capture imaging system.

11. The play environment of claim 1, wherein said imaging sensor comprises a stereo camera.

12. The play environment of claim 1, wherein said child is an infant.

13. The play environment of claim 12, wherein said child is an infant between the ages of 2 months and 11 months old.

14. The play environment of claim 13, wherein said mat is located on at least four load cells, wherein the at least four load cells are configured to measure ground reaction force, location of the ground reaction force, movements of the infant on the at least four load cells, or combinations thereof, wherein the ground reaction force is a sum of forces on the at least four load cells.

15. The play environment of claim 14, further comprising at least one camera that record and transmit actions of the child for analysis, wherein the actions are selected from the group consisting of head actions, left and right arm actions, left and right leg actions, torso actions, and a combination thereof.

16. The play environment of claim 15, wherein the play environment is configured to track the at least one type of movement on the mat by detecting movements of arm, body, legs, head or a combinations thereof.

* * * * *